(12) United States Patent
Riley

(10) Patent No.: US 6,466,809 B1
(45) Date of Patent: Oct. 15, 2002

(54) OXIMETER SENSOR HAVING LAMINATED HOUSING WITH FLAT PATIENT INTERFACE SURFACE

(75) Inventor: John J. Riley, Arvada, CO (US)

(73) Assignee: Datex-Ohmeda, Inc., Madison, WI (US)

(*) Notice: Subject to any disclaimer, the term of this patent is extended or adjusted under 35 U.S.C. 154(b) by 53 days.

(21) Appl. No.: 09/705,161

(22) Filed: Nov. 2, 2000

(51) Int. Cl.⁷ .................................................. A61B 5/00
(52) U.S. Cl. ...................................................... 600/344
(58) Field of Search ................................ 600/310, 322, 600/323, 340, 344

(56) References Cited

U.S. PATENT DOCUMENTS

| | | |
|---|---|---|
| 4,830,014 A | 5/1989 | Goodman et al. |
| 5,024,226 A | 6/1991 | Tan |
| 5,094,240 A | 3/1992 | Muz |
| 5,429,129 A | 7/1995 | Lovejoy et al. |
| 5,584,296 A | 12/1996 | Cui et al. |
| 5,638,593 A | 6/1997 | Gerhardt et al. ............ 29/592.1 |
| 5,776,059 A | 7/1998 | Kaestle et al. ................ 600/340 |
| 5,795,292 A | 8/1998 | Lewis et al. .................. 600/323 |
| 5,919,133 A | 7/1999 | Taylor et al. ................. 600/323 |
| 6,112,107 A | 8/2000 | Hannula ....................... 600/310 |

*Primary Examiner*—Eric F. Winakur
(74) *Attorney, Agent, or Firm*—Marsh Fischmann & Breyfogle LLP

(57) ABSTRACT

A number of embodiments of an oximeter sensor having a flat lower surface for interfacing with the patient are disclosed. Each sensor includes a laminated sensor housing. Part of a cable that interconnects the oximeter sensor with an oximeter is disposed within this laminated sensor housing. In one embodiment, a foam preform having a flat lower surface is disposed between an upper film assembly that is sealed to a lower film assembly which collectively define an oximeter sensor housing. This preform includes a slot in which the cable may be positioned. In another embodiment, the upper and lower film assemblies of the sensor housing are sealed together at a location which is at least generally coplanar with the lower extreme of the cable to provide the desired flat lower surface for the laminated oximeter sensor housing.

23 Claims, 7 Drawing Sheets

– – – – – – – – – – – – –
OXIMETER SENSOR HAVING LAMINATED HOUSING WITH FLAT PATIENT INTERFACE SURFACE

FIELD OF THE INVENTION

The present invention generally relates to the field of oximeter sensors and, more particularly, to oximeter sensors having a laminated construction.

BACKGROUND OF THE INVENTION

Information on the amount of oxygen within blood or more preferably a blood flow is desirable in many instances. This is often characterized as the oxygen content or oxygen saturation of the blood. Oximeters are able to provide this type of information and are generally well known in the art. Patient data that is used by the oximeter to determine the oxygen content/saturation is monitored/measured by an oximeter sensor that operatively interfaces with the oximeter. There are at least generally two types of oximeter sensors—invasive and non-invasive. Invasive oximeter sensors are installed within the body through an appropriate aperture. Non-invasive oximeter sensors are installed on the exterior skin of an appropriate body part such as a finger or a foot.

Oximeter sensors typically employ a pair of light sources that emit light at different wavelengths, as well as one or more optical detectors. The power for the emitter and the oximeter signal from the detector are transmitted between the sensor head and the oximeter via a round multiple conductor cable. A round cable is the preferred configuration for conductor shielding and for cable manufacture. Electrical signals are provided by the oximeter to the oximeter sensor to operate the light sources in a predetermined manner (e.g., each light source is "pulsed" in accordance with a predetermined pattern). Light from each of the light sources will either be absorbed by the blood or will pass entirely through the patient's tissue and blood for receipt by the detector(s). Electrical signals from the detector(s) are provided back to the oximeter. Information on how the light sources are being operated, the wavelengths of these two light sources, and the amount of light which passes through the blood to the detector(s) are all used by the oximeter to calculate the oxygen content/saturation of the blood. This information will then typically be displayed for review by appropriate personnel.

Various factors contribute to the overall commercial success of a given oximeter sensor. One is its cost. Another is its comfort when positioned on the relevant body part. It would be desirable to have an oximeter sensor the could be made within certain cost constraints. It would also be desirable to have an oximeter sensor that provided at least a certain degree of patient comfort and would not cause breakdown of the patient's skin when worn for long periods of time. Enhanced patient comfort can be realized by things such as the size, shape, and weight of the oximeter sensor, as well as the having the oximeter sensor interface with the patient so as to at least reduce the potential for the development of "pressure points." Uneven distribution of the forces being exerted on the patient by the oximeter sensor can contribute to the development of undesired soreness and possibly pressure necrosis on the patient's skin surface.

BRIEF SUMMARY OF THE INVENTION

The present invention generally relates to an oximeter sensor which utilizes a laminated construction and which provides a flat sensor/patient interface over at least those portions of the oximeter sensor housing which include an oximeter sensor cable. The oximeter sensor cable is used to establish an operative interface with an appropriate oximeter. Another way of characterizing the present invention is that it is directed to how a round oximeter sensor cable is interfaced with the patient's sensor site.

A first aspect of the present invention is embodied in an oximeter sensor that includes a laminated sensor housing. This laminated sensor housing is defined by first and second film assemblies which are appropriately interconnected, with the first film assembly the being that portion of the sensor housing that projects toward a body portion on which the oximeter sensor is mounted. Interconnection of the first and second film assemblies is provided by an appropriate seal, such as a heat seal or an integral adhesive film. In any case, each of the first and second film assemblies include at least one film. That is, one or both of the first and second film assemblies may in fact be defined by a plurality of individual films which may be interconnected by one or more of the above-noted techniques. It should be noted that each film within the first film assembly and each film within the second film assembly need not necessarily by of the same size, thickness, and/or shape. In one embodiment, the maximum thickness of each individual film in the first and second film assemblies is about 0.01 to about 0.04 inches.

The oximeter sensor of the first aspect of the present invention also includes an emitter assembly (e.g., one or more light sources and including a pair of light sources that emit light at different wavelengths) and a detector assembly which are each disposed between the first and second film assemblies within the oximeter sensor housing. A cable is electrically interconnected with both the emitter assembly and the detector assembly. This cable is also either connected with an oximeter or is at least interconnectable with an oximeter (directly or through one or more intermediate cables and an appropriate connector(s)). Part of this cable extends between the first and second film assemblies such that an end portion of the cable is actually disposed within the sensor housing. Notwithstanding this positioning of the cable within the sensor housing in this manner, that portion of the first film assembly which overlies this portion of the cable remains at least substantially flat. Having this type of flat profile in a laminated sensor housing construction reduces pressure concentrations and thereby enhances patient comfort.

Various refinements exist of the features noted in relation to the first aspect of the present invention. Further features may also be incorporated in the first aspect of the present invention as well. These refinements and additional features may exist individually or in any combination. The flat interface between that portion of the sensor housing which contains the cable and the body portion on which the oximeter sensor is installed is realized notwithstanding the fact that the cable is disposed within a sensor housing of a laminated construction. This cable is subject to a number of characterizations. One is that the cable is something more than a flat connector or the like. In one embodiment, the vertical extent or thickness of the cable is at least about 0.030 inches. One or more individual electrical conductors (e.g., wires) may collectively define the cable. Typically a single encasement (e.g., a piece of rubber tubing or the like) will be disposed about these plurality of individual electrical conductors, and this encasement may be of at least a generally circular cross section with a diameter that is within a range of about 0.070 inches to about 0.180 inches. The location where the cable exits the oximeter sensor housing is also relatively "close" to where the emitter or detector assembly is disposed. Consider the case where the emitter and detector assemblies are disposed along a first reference axis within the sensor housing, and where the cable extends within the oximeter sensor housing at least generally perpendicular to this first reference axis. In one embodiment, the distance between this first reference axis and the location where the cable actually exits the oximeter sensor housing, measured perpendicularly to the noted first reference axis, is no more than about 0.75 inches.

There are a number of ways of characterizing the interface between the cable and the first film assembly which again is that portion of the sensor housing which interfaces with the body portion on which the oximeter sensor is mounted. One way of characterizing this interface is that the contact between the first film assembly and the cable is at least substantially limited to being along and defining a line. Another way of characterizing this interface is that the first film assembly is not "wrapped" around the outer perimeter of the cable. Yet another way of characterizing this interface is that the first film assembly is tangent to the perimeter of the cable.

The flat profile for the first film assembly in the region where the cable is disposed within the sensor housing may be realized by incorporating one or more supports within the sensor housing that have a surface that is disposed in engagement with the first film assembly and that is at least substantially flat or planar. Once again, the first film assembly is that portion of the sensor housing which interfaces with the body portion on which the oximeter sensor is mounted. Any such support may have any number of characteristics. For instance, this support(s) may be formed of a compressible material that has a compression range of about 7 psi to about 25 psi for realizing about a 50% compression of the associated support(s). Representative materials having this characteristic include various types of foams, and low durometer thermoplastics and thermoset plastics.

The above-noted support(s) for providing a flat profile on that portion of the sensor housing which includes the cable will typically extend along at least substantially the entire length of that portion of the cable that is disposed within the oximeter sensor housing. In one embodiment, a support is disposed along at least one and more preferably along both sides of that portion of the cable that is disposed in the sensor housing, and further is preferably disposed in abutting engagement with this portion of the cable. Although the support could "cradle" the cable to maintain the cable and first film assembly in spaced relation, there may be a slot of sorts disposed between/defined by the above-noted pair of supports so as to allow the cable to actually contact the first film assembly. Preferably the first film assembly is only tangent to the cable on its "lower" extreme in this case and as noted above.

There are certain size-related features that may be incorporated into the above-noted support(s). Preferably there is a sufficient amount of the flat surface of that portion of the support that interfaces with the first film assembly so as to realize the desired effect of reducing pressure concentrations on the body portion over that portion of the sensor housing which contains the cable. In one embodiment, the minimum surface area of that portion of the support that interfaces with the first film assembly to provide the desired flat profile is about 0.05 in$^2$. Consider the embodiment where a pair of supports are disposed in spaced relation such that the cable may be disposed therebetween and engage the first film assembly along at least substantially a line. In this case the surface area of that portion of each of the supports which is disposed alongside the cable, which is flat, and which engages the first film assembly is at least about 0.025 in$^2$. Another way of characterizing the flat interface provided by that surface of the support(s) that engages the first film assembly is by its lateral extent. "Lateral" in this context means measured generally perpendicular to the length dimension or longitudinal extent of the cable. In one embodiment, the flat surface of the each support extends beyond each side of the cable by a distance that is equal to at least about ½ the diameter of the cable. "Beyond the side" means that this measurement is from a reference plane that is both tangent to the cable and perpendicular to the first film assembly, and is taken perpendicularly to this reference plane.

Another size-related feature of the support(s) is its height or thickness. Each support may extend between and interface with each of the first and second film assemblies, as may the cable. However, the support(s) is preferably of a lesser vertical extent than the cable. In one embodiment, the thickness or height of any support disposed proximate to the cable for providing the flat profile on the lower surface of the sensor housing is less than the diameter of this cable, but is greater than ⅓ of the diameter of the cable. Therefore, the second film assembly may "bulge" somewhat over that region of the sensor housing which contains with the cable.

The above-noted support(s) may be in the form of a preform or the like that is disposed between the first and second film assemblies. This preform may include a cable aperture for receiving the cable. This preform may also be a least generally L-shaped, with the cable being disposed in one leg of the "L" and with the emitter and detector assemblies being disposed within apertures formed in the other leg of the "L." Both the cable aperture, as well as the emitter and detector assembly apertures, may extend through the entire vertical extent or thickness of the preform. In one embodiment, the cable aperture is in the form of a slot that extends at least generally along a first reference axis, a first aperture for either the emitter or detector assembly is disposed on an end of this slot, a second aperture for the other of the emitter and detector assemblies is disposed in spaced relation to the first aperture, the first and second apertures are disposed along a second reference axis that is disposed at an angle relative to the first reference axis (e.g., 90 degrees to provide the above-noted "L-shaped" configuration), the preform is severed along the second reference axis between the first and second apertures, and each of the cable aperture, the first and second apertures, and the interconnecting cut between the first and second apertures extend through the entire vertical extent of the preform.

Other options exist for providing a flat interface between the oximeter sensor housing and the adjacent body portion along/over that portion of the sensor housing which contains the cable. The manner in which the first and second film assemblies are interconnected has an effect on the interface between the oximeter sensor housing and the body portion, or more specifically the profile of the first film assembly in that region of the sensor housing which contains the cable. In one embodiment, the first and second film assemblies are interconnected by least one seal. That portion out of the seal where the cable exits the oximeter sensor housing is disposed at least substantially coplanar with the interface between the cable and the first film assembly. Stated another way, there would be first and second seals between the first and second film assemblies on the opposite sides of the cable where the cable exits of the oximeter sensor housing. A reference plane that interconnects the first and second seals in this region would preferably be tangent to the cable, but at a minimum would be disposed at an elevation that was closer to that portion of the cable which interfaced with the first film assembly than the center of the cable. Yet another way of characterizing the first and second film assemblies where the cable exits the sensor housing is that the first film assembly is at least substantially flat and the second film assembly is at least generally U-shaped for providing a U-shaped aperture for receiving the cable.

DETAILED DESCRIPTION OF THE INVENTION

Figure 1:
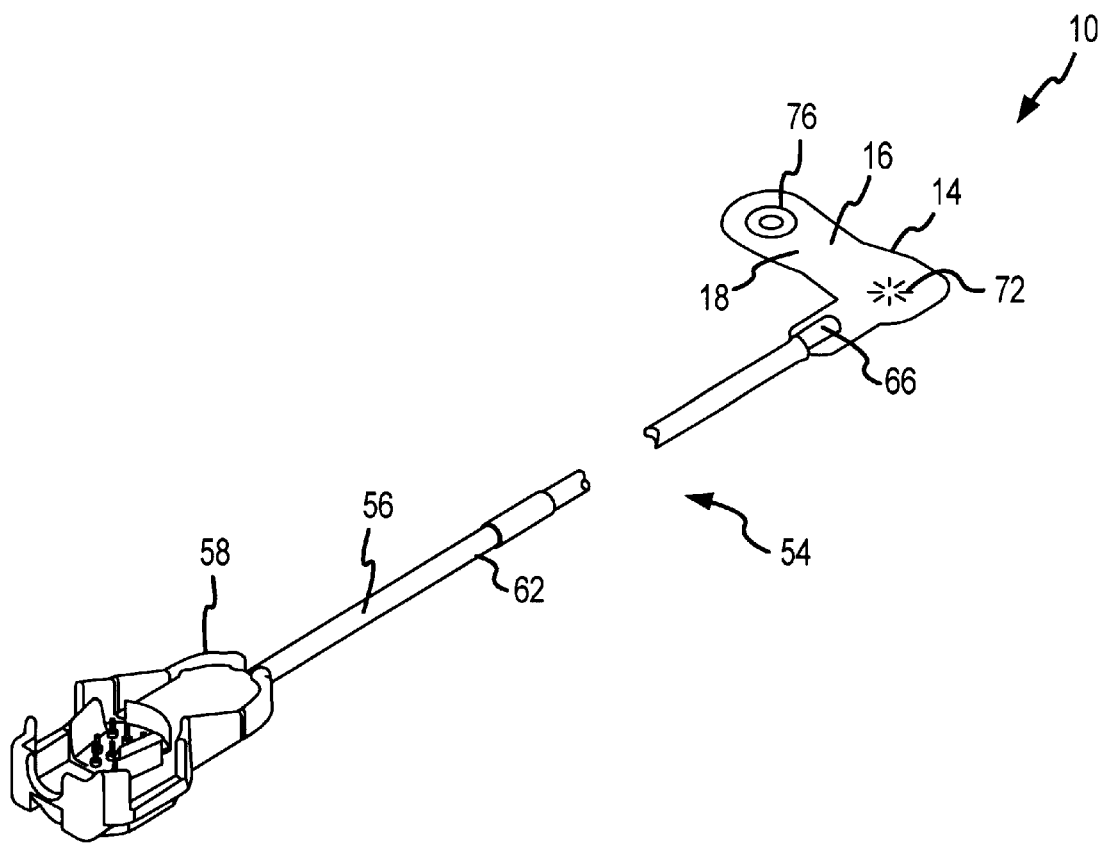
FIG. 1 is a perspective view of one embodiment of a prior art oximeter sensor.
Figure 2B:
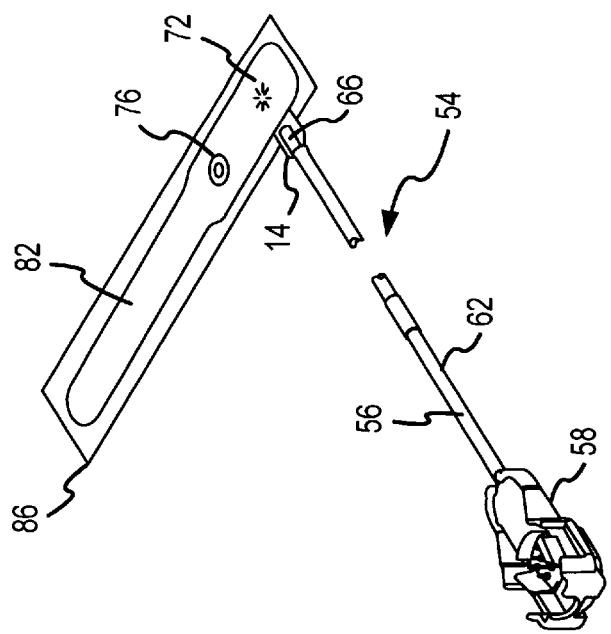
FIG. 2B is a perspective view of the oximeter sensor and attachment assembly of FIG. 2 in the assembled condition.
Figure 2A:
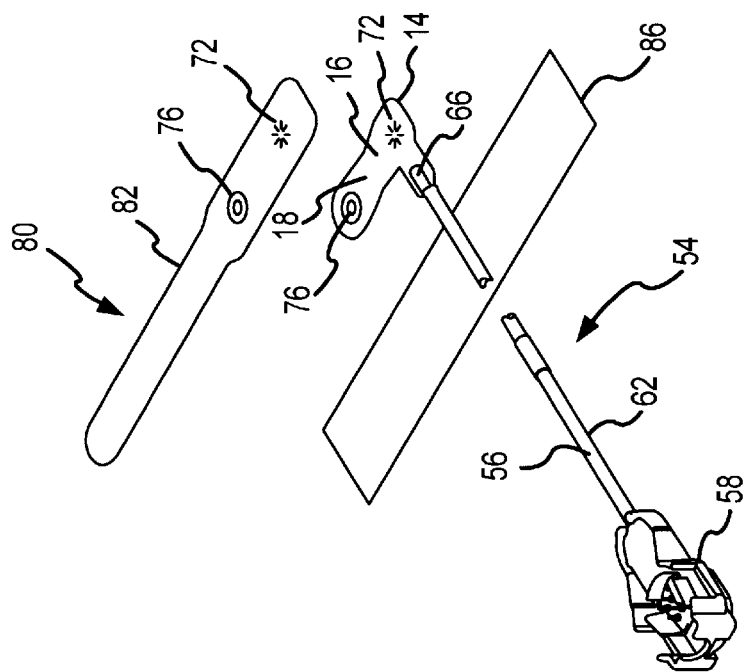
FIG. 2A is an exploded, perspective view of one embodiment of a prior art attachment assembly for securing the oximeter sensor of FIG. 1 to an appropriate body part.

The present invention will now be described in relation to the accompanying drawings which at least assist in illustrating its various pertinent features. FIG. 1 presents an oximeter sensor 10 that generally includes a sensor housing 14 and an electronics assembly 54 for providing an operative interface with an oximeter (not shown). The oximeter sensor 10 may be attached to an appropriate body part of a patient (e.g., a human, animal), such as a finger or the like. One attachment alternative for the oximeter sensor 10 is illustrated in FIGS. 2A–B in the form of an attachment assembly 80, which may be considered as being separate from or as part of the oximeter sensor 10. The attachment assembly 80 generally includes a tape 82 that has an appropriate adhesive on that surface which projects toward and engages a back side 16 of the oximeter sensor housing 14 (i.e., that side of the sensor housing 14 that is opposite a patient side 15 of the housing 14 that interfaces with the patient). Adhesive is also provided on portions of the tape 82 which extend beyond the sensor housing 14 for securing the oximeter sensor 10 to the relevant body part. In this regard, the attachment assembly 80 further includes a backing 86 which is disposed over the adhesive portions of the tape 82 and which is more preferably larger than the tape 82. This backing 86 is removable from the tape 82 to allow the oximeter sensor 10 to be disposed on the desired body part and attached in a fixed position relative thereto by the adhesive on the tape 82.

Figure 3:
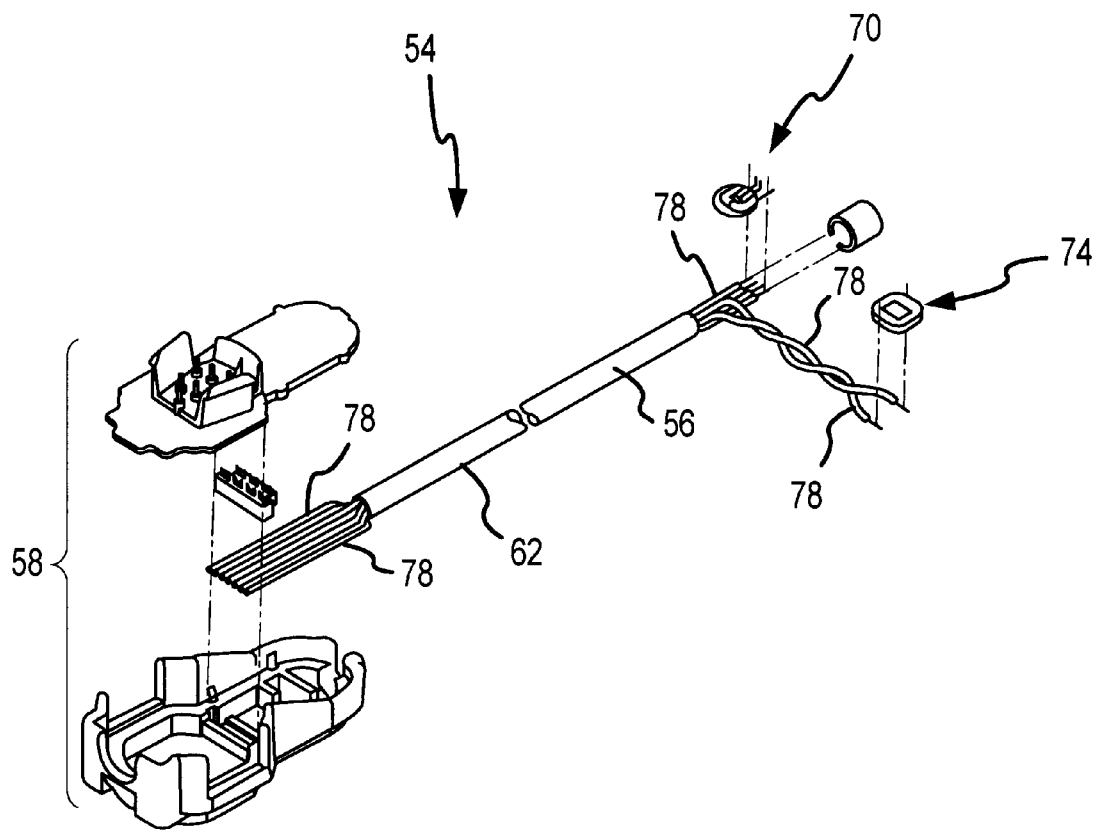
FIG. 3 is an exploded, perspective view of an electronics assembly used by the oximeter sensor of FIG. 1.

Reference now may be made to FIG. 3 in addition to FIGS. 1 and 2A–B. The electronics assembly 54 for the oximeter sensor 10 generally includes a connector 58 for providing a detachable interconnection with an oximeter, typically through one or more intermediate cables (not shown). Another part of the electronics assembly 54 is a cable 62 which is defined a plurality of individual wires 78 that are retained within an appropriate cable housing 56. One end of each of these wires 78 is appropriately electrically interconnected with an electrical contact(s) on the connector 58. The opposite ends of these wires electrically interface with either an emitter assembly 70 or a detector assembly 74 of the electronics assembly 54 of the oximeter sensor 10. The emitter assembly 70 will typically include at least two light sources (e.g., LEDs). Typically each light source of the emitter assembly 70 will emit light at a different wavelength. Both the emitter assembly 70 and detector assembly 74 are disposed within the sensor housing 14 of the oximeter sensor 10. Their locations within the sensor housing 14 may be identified by a graphical emitter indicator 72 and a graphical detector indicator 76 which may be provided on one or both of the back side 16 of the sensor housing 14 and on the non-adhesive side of the tape 82 as well.

Figure 4:
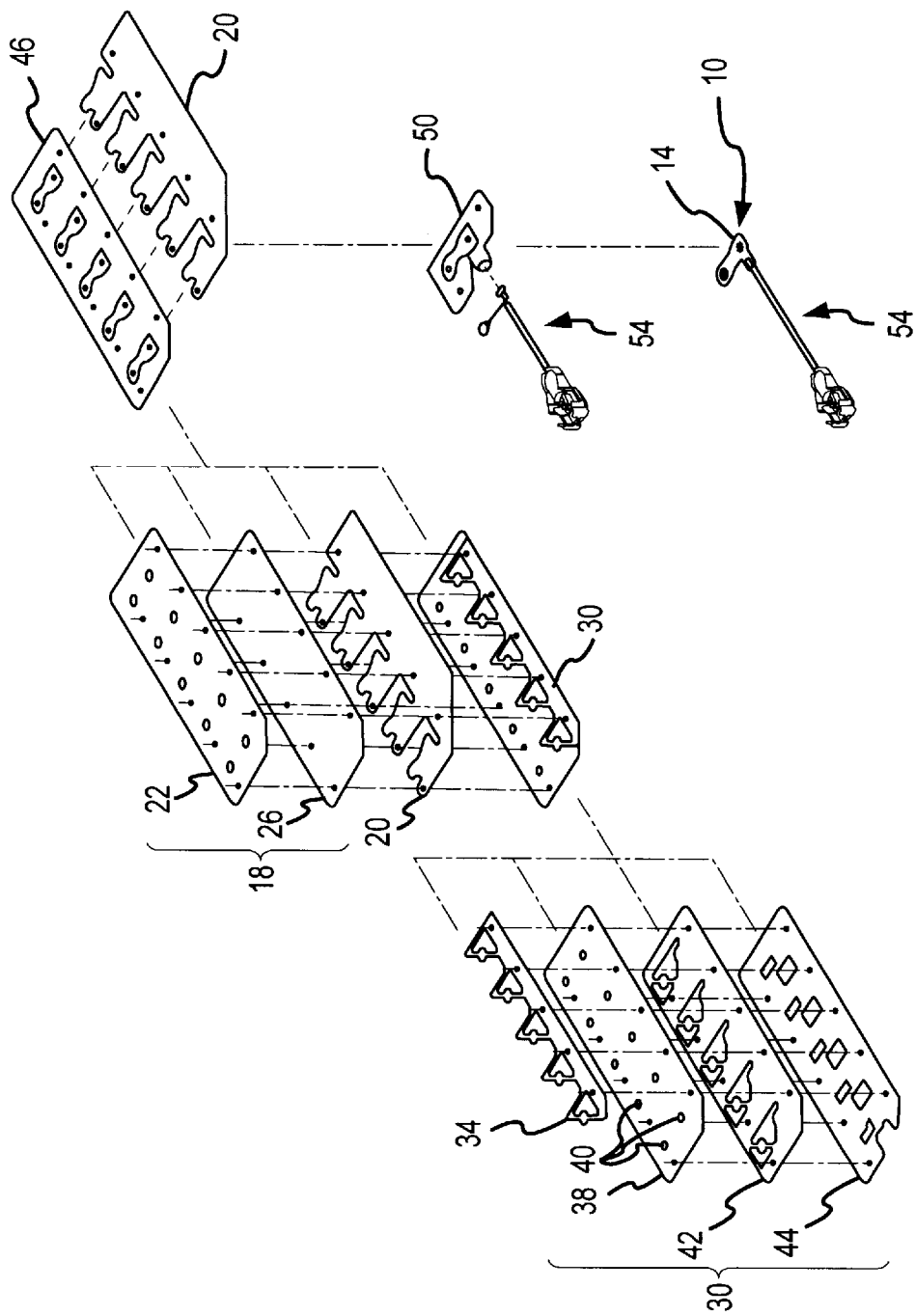
FIG. 4 is an exploded, perspective view of the laminated structure of a sensor housing used by the oximeter sensor of FIG. 1.

The sensor housing 14 of the oximeter sensor 10 of FIG. 1 utilizes a laminated construction. One embodiment of a prior art laminated construction is illustrated in FIG. 4 in the form of a laminate 46 from which one or more sensor housings 14 may be simultaneously formed. The laminate 46 includes an upper film assembly 18 (and which defines the back side 16 of the sensor housing 14) that is appropriately secured to a lower film assembly 30 (and that defines the patient side 15 of the sensor housing 14). Each sensor housing 14 formed from the laminate 46 will thereby also have an upper film assembly 18 and lower film assembly 30 as hereafter described. Both the upper film assembly 18 and the lower film assembly 30 may include one or more films. These films may have a number of characteristics. In one embodiment, each film has a thickness which is within a range of about 0.01 inches to about 0.04 inches with a preferable maximum thickness of about 0.020 inches, and in one embodiment each film is formed from an at least substantially pliable material which may be quantified as follows: 0.020 inch thick, either clear or opaque, with a 30 to 60 Type A Durometer.

The upper film assembly 18 of FIG. 4 includes a first film 22 and a second film 26. In one embodiment, the first film 22 is a polyethylene extruded film which provides both a light blocking and electrical isolation function (e.g., the first film 22 electrically isolates the oximeter sensor 10 from the patient and/or attending personnel). The surface of the first film 22 which is opposite that which interfaces with the second film 26, and further which defines the back side 16 of the sensor housing 14, preferably allows for the printing of certain images thereon, such as the above-noted emitter indicator 72 and a detector indicator 76 to at least generally identify the location of the emitter assembly 70 and a detector assembly 74, respectively, within the sensor housing 14. This is particularly useful when installing the oximeter sensor 10 on the patient. The second film 26 of the upper film assembly 18 may also provide a light blocking and electrical isolation function. In one embodiment, the second film 26 is an opaque pink thermoplastic elastomer (e.g., Krayton).

The lower film assembly 30 generally includes a third film 34, a fourth film 38, a fifth film 42, and a sixth film 44. In one embodiment, the third film 34 is a clear thermoplastic elastomer (e.g., Krayton) that reduces heat transfer between the emitter assembly 70 and the body part on which the oximeter sensor 10 is mounted, and further provides an electrical isolation function as well. The fourth film 38 is disposed between the emitter and detector assemblies 70, 74 and the body part on which the oximeter sensor 10 is mounted. In order to allow for both the passage of light from the emitter assembly 70 to the body part and from the to body part back to the detector assembly 74, the fourth film 38 includes a plurality of apertures 40. Each sensor housing 14 has an aperture 40 for each of the emitter assembly 70 and detector assembly 74. In one embodiment, the fourth film 38 is an opaque pink thermoplastic elastomer (e.g., Krayton).

The lower film assembly 30 further includes the fifth film 42 that is disposed over the fourth film 38 and which defines a cover of sorts for the emitter assembly 70 and detector assembly 74. In one embodiment, the fifth film 42 is a clear thermoplastic elastomer to allow for the passage of light therethrough (e.g., Krayton). An additional function that may be provided by the fifth film 42 is as a thermal barrier. Finally, the lower film assembly 30 includes the sixth film 44. That surface of the sixth film 44 which is opposite that which interfaces with the fifth film 42 includes an appropriate adhesive, as well as an appropriate removable liner or backing for exposing this adhesive when installation of the oximeter sensor 10 on the body part is desired (not shown). That is, the exterior surface of the sixth film 44 defines the patient side 15 of the sensor housing 14. One way in which the laminate 46 may be formed is by sealing the third film 34, fourth film 38, fifth film 42, and sixth film 44 together, and thereafter simultaneously sealing the first film 22 and the second film 26 of the upper film assembly 18, together with the pre-sealed lower film assembly 30. In this assembly procedure, it may be desirable to use one or more seal inhibitor films 20 to prevent adjacent films from sealing together at undesired locations and at undesired times.

After the various films of the upper film assembly 18 and the lower film assembly 30 have been appropriately interconnected to define the laminate 46, a cutting or stamping operation may be executed on the laminate 46 to define one or more die 50. Each die 50 includes a single sensor housing 14 and is "unsealed" over at least a portion thereof to allow for insertion of the corresponding emitter assembly 70 and detector assembly 74 within the interior of the first die 50 between its corresponding upper film assembly 18 and lower film assembly 30. Another cutting and sealing operation is executed on each die 50 after installation of the emitter assembly 70 and the detector assembly 74 to define an oximeter sensor 10 therefrom.

Figure 5:
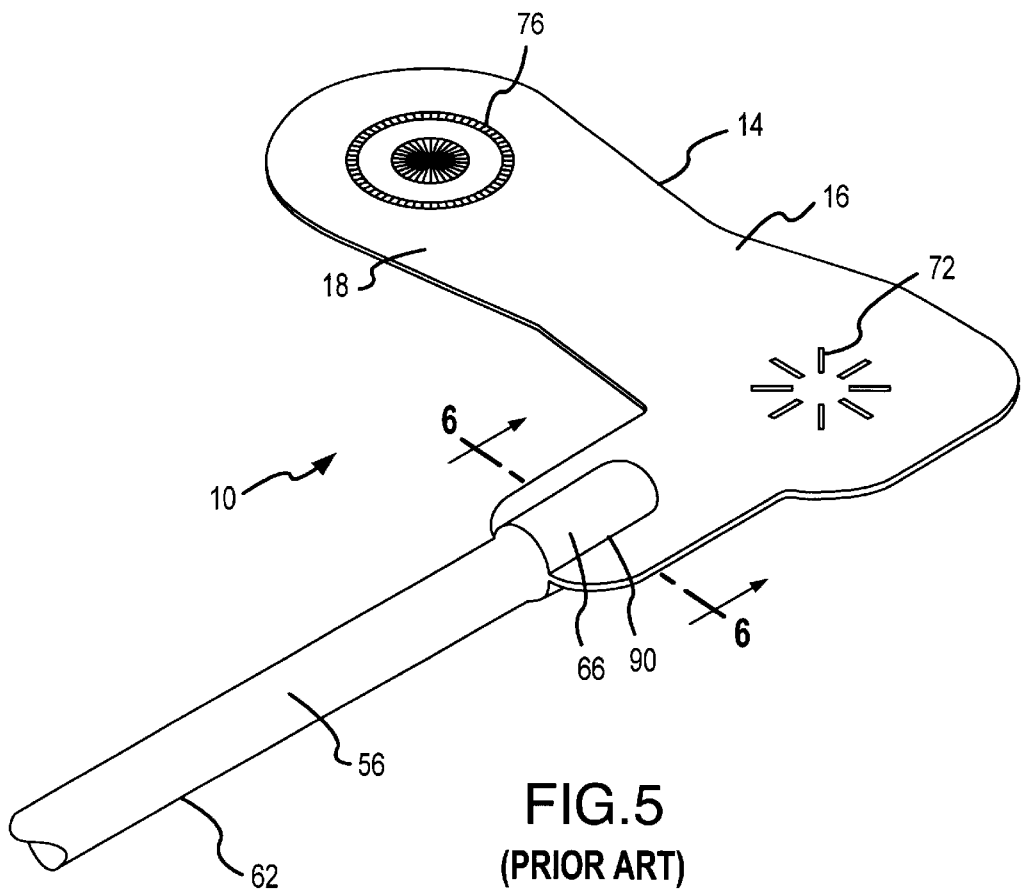
FIG. 5 is an enlarged, perspective view of the location where a cable of the electronics assembly of FIG. 3 enters the sensor housing of the oximeter sensor of FIG. 1.
Figure 6:
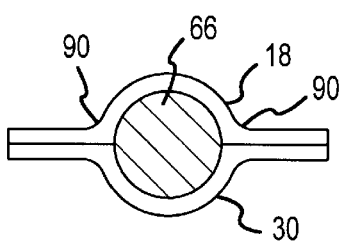
FIG. 6 is a cross-sectional view taken along line 6—6 of FIG. 5.

FIGS. 5–6 illustrates that a section 66 of the cable 62 extends within the sensor housing 14, which includes the cable housing 56 for retaining the plurality of wires 78 therewithin. There are a number of notables in relation to this feature of the prior art oximeter sensor 10. Initially, the upper film assembly 18 and lower film assembly are joined by a seal 90. This seal 90 between the upper film assembly 18 and the lower film assembly 30 is disposed at least substantially coplanar with a location that corresponds with the "horizontal midpoint" of the cable 62. As result, the cable 62 bulges both the upper film assembly 18 and the lower film assembly 30 in opposite directions and in equal amounts. In the case of the lower film assembly 30, the bulging caused by the cable 62 is of course in the direction of the body part on which the oximeter sensor 10 is mounted. Bulging of the lower film assembly 30 in this manner may provide an uncomfortable interface between the oximeter sensor 10 and the body part on which the sensor 10 is mounted due to pressure concentrations caused by the uneven surface that exists on the lower film assembly 30 over that region which includes the cable 62.

Figure 7:
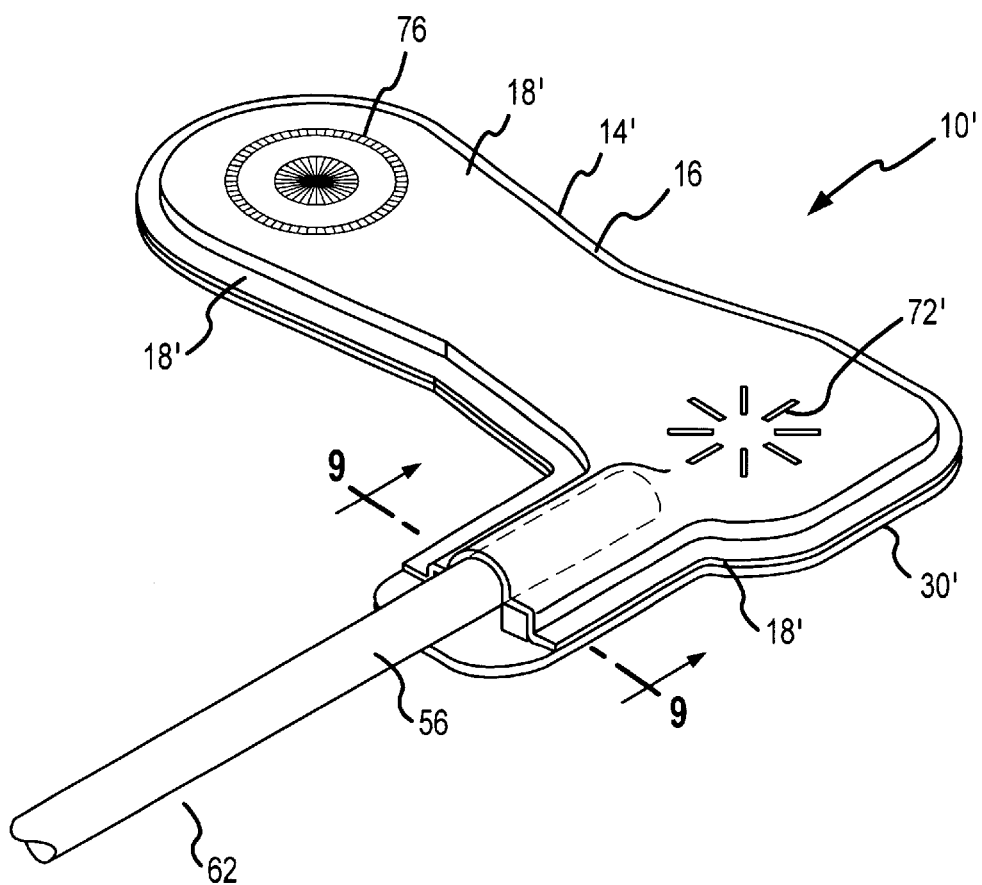
FIG. 7 is a perspective view of an oximeter sensor that provides a flat interface over that portion of a cable of an electronics assembly that is disposed within a sensor housing of the oximeter sensor.
Figure 8:
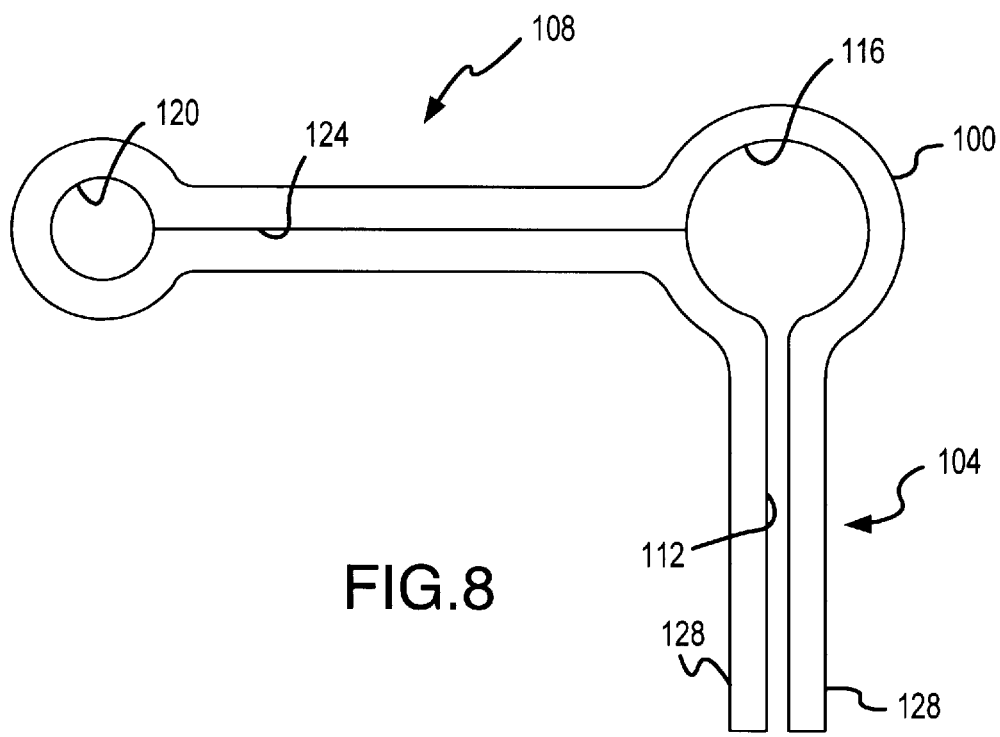
FIG. 8 is a top, plan view of a preform that is disposed within the sensor housing of the oximeter sensor of FIG. 7.
Figure 9:
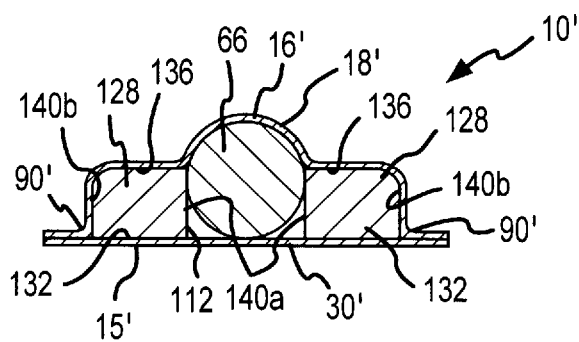
FIG. 9 is a cross-sectional view taken along line 9—9 in FIG. 7.

FIGS. 7–9 present one embodiment of an oximeter sensor 10' that enhances the patient interface over that portion of the sensor housing 14 which includes the cable 62. Components of the oximeter sensor 10' of FIGS. 7–9 having corresponding components in the oximeter sensor 10 of FIGS. 1–6 are identified by the same reference numeral. Those components which differ in a least some respect, however, include a "single prime" designation in the embodiment of FIGS. 7–9. Generally, the primary distinction between the oximeter sensor 10' of FIGS. 7–9 and the oximeter sensor 10 of FIGS. 1–6 is the inclusion of a preform 100 between the upper film assembly 18' and the lower film assembly 30'. The preform 100 modifies the profile of both the upper film assembly 18' and lower film assembly 30', and therefore each includes the noted "single prime" designation. It is this preform 100 that provides an at least substantially flat profile on the patient side 15' of the sensor housing 14' over/throughout that region which includes the cable 62, and thereby enhances the patient interface in this region in relation to reducing the unit pressure that is exerted on the patient when the oximeter sensor 10' is attached to the relevant body part.

The preform 100 has an at least generally L-shaped profile which is evident by the "bulge" in the upper film assembly 18' in FIG. 7 and by the plan view of the preform 100 that is presented in FIG. 8. One "leg" of this L-shaped profile is provided by a cable section 104 of the preform 100. The opposite "leg" of the preform 100 is provided by an emitter/detector section 108. In the illustrated embodiment, the cable section 104 and the emitter/detector section 108 are least substantially transversely disposed to provide the noted L-shaped profile. Other relative orientations could be utilized.

The cable section 104 of the preform 100 includes a cable aperture or slot 112 for housing the sensor housing section 66 of the cable 62. Disposed on one end of this cable aperture 112 is an emitter assembly aperture 116. The emitter assembly aperture 116 is disposed within the emitter/detector section 108 of the preform 100 and houses the emitter assembly 70. Individual wires 78 for both the emitter and detector assemblies 70, 74 extend beyond the end of the cable housing 56 of the cable 62 and into the emitter assembly aperture 116. Certain of these wires 78 are electrically interconnected with the emitter assembly 70, while those wires 78 which are associated with the detector assembly 74 extend along/within a cut 124 formed in the preform 100 to a detector assembly aperture 120 in the opposite end of the emitter/detector section 108. It should be appreciated that the cut 124 could be "wider" or in the form of a slot, although such is not currently required for housing the wires 78 that provide communication with the detector assembly 74. In fact, the cut 124 and the use of a compressible material for the preform 100 may provide for a more secure engagement of the wires 78 therewithin to keep the same in a desired position. In any case, the detector assembly 74 is disposed in the detector assembly aperture 120 and is electrically interconnected with the wires 78 which extend along the cut 124 to the detector assembly aperture 120. The emitter assembly aperture 116 and the detector assembly aperture 120 are therefore disposed in spaced relation on the emitter/detector section 108 of the preform 100 along a reference axis, which in turn is disposed at an angle relative to the longitudinal extent of the cable aperture 112 (e.g., 90 degrees in the illustrated embodiment).

The detector assembly aperture 120, the cut 124, the emitter assembly aperture 120, and the cable aperture 112 each extend through the entire vertical extent of the preform 100 in the illustrated embodiment. This allows the preform 100 to be formed from a simple die cutting operation or the like. Representative materials which may be readily formed into the shape illustrated in FIG. 8 and including in the noted manner, as well as which provide one or more other desirable characteristics for use in the oximeter sensor 10', include foam, and low durometer (e.g., less than 50 A) thermoplastics and thermoset plastics. One currently preferred material for the preform 100 is a cross-linked polyethylene foam.

Advantages of the above-described emitter/detector section 108 of the preform 100 include enhancing the retention of the emitter and detector assemblies 70, 74 in a predetermined location, protecting the emitter and detector assemblies 70, 74 from shock or impact when disposed within the sensor housing 14', and providing a flat interface on the patient side 15' of the sensor housing 14'. The primary function of the cable section 104 of the preform 100 is for providing an at least substantially flat surface on the patient side 15' the sensor housing 14' over at least that the region that contains the cable 62 and as illustrated in FIG. 9 (e.g., the profile illustrated in FIG. 9 exists over the entire "length" of the cable 62 that is disposed in the sensor housing 14').

The cable section 104 of the preform 100 may be characterized as being defined by a pair of laterally-spaced supports 128 which terminate at that portion of the preform 100 which defines the emitter assembly aperture 116. "Lateral" in this sense means perpendicular to the longitudinal extent of the cable 62 within the sensor housing 14', or stated another way perpendicular to the longitudinal extent of the cable aperture 112. In one embodiment, the supports 128 are separated by a space which is at least generally equal to the diameter of the cable 62, but possibly slightly less than the diameter of the cable 62 so as to slightly compress the supports 128 when the cable 62 is disposed within the cable aperture 112. Each support 128 includes a lower surface 132 that is at least substantially flat or planar, and that directly interfaces with the lower film assembly 30'. The entire lower surface of the preform 100 is in fact preferably flat and thereby coplanar with the lower surface 132. The flat profile of the patient side 15' of the sensor housing 14' over that portion occupied by the cable 62 is clearly illustrated in FIG. 9. The interior of the lower film assembly 30 is at least substantially tangent to the exterior surface of the cable 62. Stated another way, the contact between the cable 62 and the lower film assembly 30' is limited to being at least substantially a line contact. Each support 128 also includes an upper surface 136 that directly interfaces with the upper film assembly 18'. The lower surface 132 and upper surface 136 of the supports 128 are thereby disposed in vertically spaced relation and define a thickness or height of the corresponding support 128.

Extending between the upper surface 136 and lower surface 132 of each support 128 is a pair of side surfaces 140. The side surface 140a of each support 128 interfaces with the cable 62 when disposed within the cable aperture 112. Preferably the supports 128 are at least slightly compressed when the cable 62 is disposed within the cable aperture 112. The side surface 140b is disposed in laterally spaced relation to its corresponding side surface 140a. Therefore, the distance between the side surface 140a and side surface 140b of a particular support 128 defines a width dimension of the corresponding support 128. In the illustrated embodiment, the side surfaces 140a, 140b of each support 128 are at least substantially flat or planar, and are disposed at least generally perpendicular to their corresponding lower and upper surface 132, 136. Although the orientation of the upper surface 136 and the side surfaces 140 of each support 128 do not necessarily have any effect on the provision of a flat or planar surface for the patient side 15' of the sensor housing 14' in that region occupied by the cable 62, the above-noted orientations reduce the cost for making the preform 100, which is of course desirable. Moreover, having the side surfaces 140a in a vertical orientation as shown (or possibly a converging orientation progressing from the lower film assembly 30' to the upper film assembly 18' and not shown), may facilitate the retention of the cable 62 within the cable aperture 112.

It should be appreciated that different configurations could be utilized for the side surfaces 140a of the preform 100, for instance so as to reduce or possibly entirely alleviate the space between the preform 100 and the cable 62. Other configurations could be utilized for the preform 100 as well, and which would still yield a flat or planar surface on the patient side 15' of the sensor housing 14' over that portion thereof that includes the cable 62. For instance, a concave, longitudinal recess could be formed on the upper surface of a preform, which would not extend through the entire vertical extent or thickness of the preform, and which would thereby "cradle" the cable 62 (not shown). This type of preform could then include a unitary flat surface for interfacing with the lower film assembly 30', and which would also maintain the cable 62 and the lower film assembly 30' in vertically spaced relation.

Certain characteristics may be utilized in relation to the preform 100, including any one or more of the following: 1) the material from for the preform 100 may be compressible to at least a certain extent; 2) the material which forms the preform 100 may be compressed about 50 percent when exposed to pressure that is within the range about 7 psi to about 25 psi; 3) the thickness of the cable section 104 of the preform 100 along the entire longitudinal extent of the cable aperture 112 is preferably greater than about ⅓ of the diameter of the cable 62, but is preferably less than about the diameter of the cable 62; 4) the thickness of the cable section 104 of the preform 100 along the entire longitudinal extent of the cable aperture 112 may be about 0.060 inches; 5) the preform 100 may have a uniform thickness or height throughout the entirety thereof; 6) the width of the lower surface 132 of each support 128 may be at least about 0.050 inches; 7) the width of the lower surface 132 of each support 128 may be within a range of about 0.050 inches to about 0.200 inches; 8) the area of the lower surface 132 of each support 128 may be at least about 0.025 in$^2$; 9) the area of the lower surface 132 of each support 128 may be within a range of about 0.025 in$^2$ to about 0.15 in$^2$; 10) the cable 62 may exit the sensor housing 14' a distance of no more than about 0.75 inches from a reference axis that extends through the center of the emitter assembly aperture 116 and the detector assembly aperture 120.

The preform 100 is a substantial contributor to realizing a flat profile over that region of the patient side 15' of the sensor housing 14' having the cable 62 disposed therein. Another feature of the sensor housing 14' which also contributes to realizing this flat profile is the manner in which the upper film assembly 18' is secured to the lower film assembly 30'. Referring to FIG. 9, the upper film assembly 18' is secured to the lower film assembly 30' along a seal 90'. This seal 90' exists on both sides of the preform 100 where the cable 62 exits the sensor housing 14'. Generally and at least in this region, this seal 90' is disposed at least substantially co-planar with the interface between the upper film assembly 18' and the lower film assembly 30'. That is, a reference line or plane which extends through or contains the seal 90' on each side of the cable 62 would be tangent to the lower extreme of the cable 62.

Figure 10:
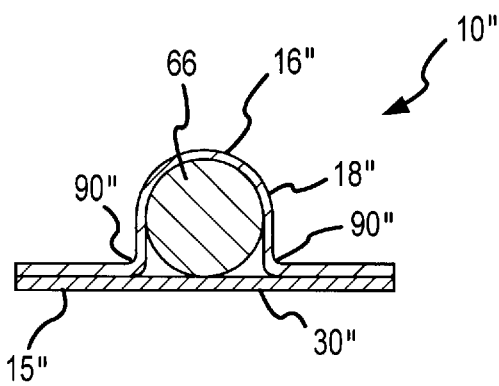
FIG. 10 is a cross-sectional view of another embodiment of an oximeter sensor that provides a flat interface over that portion of a cable of an electronics assembly that is disposed within a sensor housing of the oximeter sensor.

Another embodiment of an oximeter sensor 10" that provides a flat interface on the patient side of a laminated sensor housing in the region having the cable is illustrated in FIG. 10. Components of the oximeter sensor 10" of FIG. 10 having corresponding components in the oximeter sensor 10 of FIGS. 1–6 are identified by the same reference numeral. Those components which differ in a least some respect, however, include a "double prime" designation in the embodiment of FIG. 10. Only those portions of the oximeter sensor 10" which illustrate how the flat profile is realized are illustrated in FIG. 10. All other components of the oximeter sensor 10" can be assumed to be the same as those of the oximeter sensor 10 of FIGS. 1–6.

The primary distinction between the oximeter sensor 10" of FIGS. 10 and the oximeter sensor 10 of FIGS. 1–6 relates to the location of the seal 90" which interconnects the upper film assembly 18" and the lower film assembly 30". As in the case of the embodiment of FIGS. 7–9, the upper film assembly 18" is secured to the lower film assembly 30" along a seal 90" that is disposed in a different location than the seal 90 of FIGS. 1–6. In the case of the FIG. 10 embodiment, the seal 90" exists on both sides of the preform 100 where the cable 62 exits the sensor housing 14". Generally and at least in this region, the seal 90" on each side of the cable 62 is disposed at least substantially co-planar with the interface between the upper film assembly 18" and the lower film assembly 30". That is, a reference line or plane which extends through or contains the seal 90' on each side of the cable 62 would be tangent to the lower extreme of the cable 62.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. An oximeter sensor which comprises:
 a laminated sensor housing which comprises first and second film assemblies which are interconnected, wherein said first film assembly projects toward a body portion of a patient when said oximeter sensor is in use;
 an emitter assembly which is sandwiched between said first and second film assemblies;
 a detector assembly which is sandwiched between said first and second film assemblies in spaced relation to said emitter assembly; and
 a cable which is electrically interconnected with each of said emitter assembly and said detector assembly and which is at least electrically interconnectable with an oximeter, wherein a first portion of said cable is sandwiched between said first and second film assemblies, wherein a second portion of said cable extends beyond said sensor housing, and wherein said first film assembly is at least substantially flat throughout an area which overlies said first portion of said cable.

2. An oximeter sensor, as claimed in claim 1, wherein:
each of said first and second film assemblies comprises least one film, wherein a maximum thickness of any said film of either of said first and second film assemblies is 0.020 inches.

3. An oximeter sensor, as claimed in claim 1, wherein:
said emitter assembly comprises first and second light sources which emit light at different wavelengths.

4. An oximeter sensor, as claimed in claim 1, wherein:
said first portion of said cable interfaces with said first film assembly at least substantially only along a line.

5. An oximeter sensor, as claimed in claim 1, wherein:
said first film assembly is at least substantially tangent to said first portion of said cable.

6. An oximeter sensor, as claimed in claim 1, wherein:
said sensor housing comprises a first seal between said first and second film assemblies, wherein said first seal extends between first and second seal ends, wherein a space between said first and second seal ends defines a first opening which provides an access to an interior of said sensor housing which is defined at least in part by said first and second film assemblies, wherein said first portion of said cable extends between said first and second film assemblies through said first opening.

7. An oximeter sensor, as claimed in claim 1, wherein:
said sensor housing further comprises a first support which is disposed between said first and second film assemblies, which comprises a first surface which is disposed in interfacing relation with said first film assembly, and which comprises a second surface which extends away from said first surface and at least generally toward said second film assembly, wherein said first surface is flat, and wherein at least part of said first portion of said cable is disposed in abutting engagement with at least part of said second surface of said first support.

8. An oximeter sensor, as claimed in claim 7, wherein:
said first support is foam having a compression range of about 7 psi to about 25 psi for about a 50% compression of said first support.

9. An oximeter sensor, as claimed in claim 1, wherein:
said sensor housing comprises first and second laterally spaced supports which extend between said first and second film assemblies, wherein said first and second laterally spaced supports each comprise a first surface which is disposed in interfacing relation with said first film assembly, wherein said first surface of each of said first and second supports is flat, and wherein said first portion of said cable is retained between said first and second laterally spaced supports.

10. An oximeter sensor, as claimed in claim 9, wherein:
said first and second supports are each a foam having a compression range of about 7 psi to about 25 psi for about a 50% compression of said first and second supports.

11. An oximeter sensor, as claimed in claim 9, wherein:
said first portion of said cable is defined by a first diameter, wherein a thickness of each of said first and second supports between said first and second film assemblies is greater than one-third of a magnitude of said first diameter and is less than said magnitude of said first diameter.

12. An oximeter sensor, as claimed in claim 9, wherein: a surface area of said first surface of each of said first and second supports is at least about 0.025 in$^2$.

13. An oximeter sensor, as claimed in claim 9, wherein: said first surface of each of said first and second supports each have a width of at least about 0.05 inches, wherein a width dimension of said first surface and each of said first and second supports is measured perpendicularly to a longitudinal extent of said first portion of said cable within said sensor housing.

14. An oximeter sensor, as claimed in claim 9, wherein: a vertical extent of each of said first and second supports is at least about 0.050 inches.

15. An oximeter sensor, as claimed in claim 9, wherein: said cable extends vertically beyond each of said first and second supports in a direction of said second film assembly.

16. An oximeter sensor, as claimed in claim 1, wherein: said sensor housing farther comprises a preform, wherein said preform is disposed between said first and second film assemblies, wherein said preform comprises a cable aperture, wherein said preform comprises a first surface which is flat and which interfaces with said first film assembly, and wherein said first portion of said cable is disposed within said cable aperture of said preform.

17. An oximeter sensor, as claimed in claim 16, wherein: said preform is at least generally L-shaped, wherein said first portion of said cable is disposed in a first leg of said preform, and wherein said emitter and detector assemblies are disposed in a second leg of said preform.

18. An oximeter sensor, as claimed in claim 17, wherein: said cable aperture extends entirely through said first leg of said preform;
said preform comprises a first aperture which extends entirely through said second leg of said preform and which is interconnected with an end of said cable aperture;
said preform comprises a second aperture which extends entirely through said second leg of said preform and which is disposed in spaced relation to said first aperture;
one of said emitter assembly and detector assemblies is disposed in said first aperture and the other of said emitter and detector assemblies is disposed in said second aperture; and
said first and second apertures are interconnected by at least a cut which extends entirely through said second leg of said preform.

19. An oximeter sensor, as claimed in claim 16, wherein: said cable aperture is a slot which extends entirely through said preform, whereby said first portion of said cable still directly interfaces with said first film assembly.

20. An oximeter sensor, as claimed in claim 1, wherein: a seal between said first and second film assemblies in proximity to where said cable exits said sensor housing is disposed at least substantially coplanar with an interface between said first portion of said cable and said first film assembly.

21. An oximeter sensor, as claimed in claim 1, wherein: said first portion of said cable is circular such that a center of said cable is disposed midway between said first and second film assemblies at said first portion of said cable, wherein a seal between said first and second film assemblies in proximity to where said cable exits said sensor housing is disposed at an elevation which is closer to an elevation of that portion of said first portion of said cable which interfaces with said first film assembly than an elevation of said center of said cable.

22. An oximeter sensor, as claimed in claim 1, wherein: said first and second film assemblies collectively define a U-shaped aperture through which said cable extends into said sensor housing.

23. An oximeter sensor, as claimed in claim 1, wherein: said emitter assembly and said detector assembly are each disposed at least generally along a first reference axis, wherein said cable exits said sensor housing at a distance which is no more than about 0.75 inches from said first reference axis along a line which is perpendicular to said first reference axis.

* * * * *

UNITED STATES PATENT AND TRADEMARK OFFICE
CERTIFICATE OF CORRECTION

PATENT NO. : 6,466,809 B1
DATED : October 15, 2002
INVENTOR(S) : Riley

It is certified that error appears in the above-identified patent and that said Letters Patent is hereby corrected as shown below:

<u>Column 13,</u>
Line 22, delete the word "farther", and insert therefor -- further --.

Signed and Sealed this

Twenty-eighth Day of January, 2003

JAMES E. ROGAN
*Director of the United States Patent and Trademark Office*